United States Patent [19]
Chojkier et al.

[11] Patent Number: 6,147,123
[45] Date of Patent: Nov. 14, 2000

[54] TREATMENT AND PREVENTION OF HEPATIC DISORDERS

[75] Inventors: Mario Chojkier, San Diego; Dennis Carson, Del Mar, both of Calif.

[73] Assignee: The Regents of the University of California, Calif.

[21] Appl. No.: 09/274,624

[22] Filed: Mar. 23, 1999

Related U.S. Application Data

[62] Division of application No. 08/723,052, Sep. 30, 1996.

[51] Int. Cl.[7] .............................. A61K 31/05; C07C 39/04
[52] U.S. Cl. ........................ 514/731; 568/716; 568/780; 514/893; 514/894
[58] Field of Search ..................................... 514/731, 893, 514/894; 568/716, 780

[56] References Cited

PUBLICATIONS

McCrmick, D.L. et al.: Anticarcinogenic and hepatotoxic interactions between Retinyl Acetate and Butylated Hydroxytoluene in rats. Cancer Res. vol. 46, pp. 5264–5269, 1986.

*Primary Examiner*—John Kight
*Assistant Examiner*—Charanjit S. Aulakh
*Attorney, Agent, or Firm*—Medlen & Carroll, LLP

[57] ABSTRACT

New methods are described for the treatment of viral hepatitis C involving the administration of vitamin E and other compounds with antioxidant properties. Treatment with high doses of vitamin E is effective in treating chronic hepatitis C in patients refractory to interferon. In addition, new methods are described for the treatment of hepatic fibrosis and hepatic conditions manifesting hepatic fibrosis involving the administration of butylated hydroxytoluene and a metabolite of pentoxifylline, 1-[3-carboxypropyl]-3, 7-dimethylxanthine.

2 Claims, 13 Drawing Sheets

Pentoxifylline                    Metabolite 5

MDA

Hepatitis C

MDA

Hepatitis C
+
d-α-tocopherol

α-SMA

Hepatitis C

α-SMA

Hepatitis C
+
d-α-tocopherol

Col α1(I) mRNA

Hepatitis C

Col α1(I) mRNA

Hepatitis C
+
d-α-tocopherol

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

GGGGACTTTC CC                                        12

(2) INFORMATION FOR SEQ ID NO:2:

```
    (i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

GATCATAAGC AGCTGAACTG CC                                          22

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GCCCGGAGAC CCCGACAC                                               18

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GTGTCGGGGT CTCCGGGC                                               18
```

TREATMENT AND PREVENTION OF HEPATIC DISORDERS

This is a divisional of application Ser. No. 08/723,052, filed Sep. 30, 1996.

This invention was made with government support under GM47165 and DK 38652 awarded by the National Institutes of Health. The government has certain rights in this invention.

FIELD OF THE INVENTION

The present invention relates generally to the treatment and prevention of hepatic fibrosis, and more particularly to the administration of pharmacologically active compounds for the treatment and prevention of viral hepatitis C.

BACKGROUND OF THE INVENTION

The majority of patients suffering from chronic hepatitis are infected with either chronic hepatitis B virus (HBV), chronic hepatitis C virus (HCV) or autoimmune disease. While each type is associated with certain distinct characteristics, generally speaking, chronic hepatitis can progress to cirrhosis and hepatic failure. Unfortunately, there are few effective treatments for hepatitis. For example, treatment of autoimmune chronic hepatitis is generally limited to immunosuppressive treatment with corticosterioids. For the treatment of hepatitis B and C, the FDA has approved administration of recombinant interferon alpha. However, interferon alpha is associated with a number of dose-dependent adverse effects, including thrombocytopenia, leukopenia, bacterial infections, and influenza-like symptoms. Indeed, normal interferon alpha dosing parameters for the treatment of chronic hepatitis B require discontinuance or dosing adjustment in approximately 20–50% of patients. Other agents used to treat chronic hepatitis B or C include the nucleoside analog ribovirin and ursodeoxycholic acid; however, neither has been shown to be very effective. [See Medicine, (D. C. Dale and D. D. Federman, eds.) (Scientific American, Inc., New York), 4:VIII: 1–8 (1995)].

Indeed, current therapies do not effectively prevent or cure hepatitis C or the hepatic fibrosis associated with the disease. Clearly, new alternative treatment methods and agents are needed and would be welcomed by those plagued by hepatitis C who either cannot tolerate available treatment regimens or who are refractory to those regimens.

SUMMARY OF THE INVENTION

The present invention discloses the administration of vitamin E and other pharmacologically active compounds for the treatment and prevention of viral hepatitis C and other chronic liver diseases. Indeed, treatment with high doses of vitamin E may be effective in treating chronic hepatitis C in patients refractory to interferon.

The present invention also describes new methods for the treatment and prevention of hepatic fibrosis and hepatic conditions manifesting hepatic fibrosis involving the administration of compounds with antioxidant properties. In preferred embodiments, these new methods involve the administration of butylated hydroxytoluene and a metabolite of pentoxifylline, 1-[3-carboxypropyl]-3, 7-dimethylxanthine (metabolite 5 of pentoxifylline).

Specifically, the present invention contemplates a method of treating hepatitis C, comprising: a) providing i) a subject having symptoms of hepatitis C, and ii) an antioxidant; and b) administering a therapeutic amount of the antioxidant to the subject under conditions such that the symptoms are diminished. In one embodiment, the subject is refractory to interferon. In some embodiments, the antioxidant is administered orally to the subject, whereas it is administered parenterally in other embodiments. In further embodiments, the antioxidant is d-α-tocopherol. In some embodiments, the method further comprises the step prior to step b) of measuring the symptoms by liver biopsy; moreover, some embodiments of the method further comprise the step subsequent to step b) of measuring the symptoms by liver biopsy.

The present invention also contemplates a method of treating hepatitis C, comprising: a) providing i) a subject with hepatitis C having symptoms indicating fibrosis, and ii) d-α-tocopherol; and b) administering a therapeutic amount of d-α-tocopherol to the subject under conditions such that the symptoms are diminished. In particular embodiments, the subject is refractory to interferon. In certain embodiments, the d-α-tocopherol is administered orally to the subject, while it is administered parenterally in other embodiments. When administered orally, the therapeutic amount of d-α-tocopherol is from 800 units daily to 1600 units daily in preferred embodiments, and from 1000 units daily to 1400 units daily in more preferred embodiments. In some embodiments, the method further comprises the step prior to step b) of measuring the symptoms by liver biopsy. Moreover, some embodiments of the method further comprise the step subsequent to step b) of measuring the symptoms by liver biopsy.

As indicated above, the present invention also contemplates the administration of other antioxidants for the treatment of hepatic fibrosis. For example, the present invention contemplates a method of treating hepatic fibrosis, comprising: a) providing i) a subject with hepatic fibrosis, and ii) 1-[3-carboxypropyl]-3, 7-dimethylxanthine or butylated hydroxytoluene; and b) administering a therapeutic amount of 1-[3-carboxypropyl]-3, 7-dimethylxanthine or butylated hydroxytoluene to the subject under conditions such that the hepatic fibrosis is diminished. In particular embodiments, the 1-[3-carboxypropyl]-3, 7-dimethylxanthine or butylated hydroxytoluene is administered orally to the subject. When administered orally, the therapeutic amount of the 1-[3-carboxypropyl]-3, 7-dimethylxanthine is from 400 mg daily to 1200 mg daily in some embodiments. Other embodiments and aspects of the present invention will become apparent to those skilled in the art based upon the description that follows.

DEFINITIONS

To facilitate understanding of the invention that follows, a number of terms and phrases are defined below.

The term "subject" includes humans as well as other animals.

The term "hepatitis C" refers to subjects infected with the hepatitis C virus, a single-stranded RNA virus that possesses a lipid-containing envelope and is thought to be a member of the flavivirus family. The term encompasses all forms of hepatitis C, including acute hepatitis C and all forms of chronic hepatitis C (e.g., chronic active hepatitis and chronic persistent hepatitis).

The phrase "symptoms of hepatitis C" refers broadly to clinical manifestations, laboratory and imaging results, as well as liver morphology and histology exhibited by subjects which suggest the presence of hepatitis C. Clinical manifestations may include, but are not limited to, abdominal pain, jaundice, hepatosplenomegaly, and ascites. Laboratory and imaging results may include, but are not limited to, elevated serum aminotransferase, bilirubin, and gamma-globulin levels, as well as an enlarged liver on computed tomography, magnetic resonance imaging, and hepatic ultrasonography. Hepatic morphological and histological indicators of hepatitis C may include, but are not limited to, deposition of fibrotic tissue evident through liver biopsy.

The phrases "symptoms indicating fibrosis," "hepatic fibrosis" and the like refer to hepatic morphological and histological indicators of fibrosis. Such indicators may include, but are not limited to, deposition of fibrotic tissue evident through liver biopsy and activation of the fibrogenesis cascade as evidenced by increased MDA-adducts, stellate cell activation, and enhanced expression of c-myb and collagen α1(I) mRNA in stellate cells.

The term "diminished" means that there has been a reduction in the extent of the symptoms of hepatitis C, hepatic fibrosis, etc. In general, such a reduction is demonstrated by objective indicators. For example, comparison of liver biopsy samples taken before and after administration of a therapeutic agent may indicate a reduction in fibrosis. In addition, reduction of symptoms may also be demonstrated by subjective indicators, such as a reduction in abdominal pain.

The term "oxidant" refers to the electron acceptor in an oxidation-reduction reaction [i.e., the chemical reaction whereby electrons are removed (oxidation) from atoms of the substances being oxidized and transferred to those being reduced (reduction)]. The term "antioxidant" refers to compounds and combinations of compounds that prevent the process of oxidation, thereby preventing the effects of reactive oxygen species (e.g., free radicals) that may have adverse effects on a subject. For example, antioxidants may prevent oxidation of essential cellular constituents (e.g., ubiquinone) or prevent the formation of toxic oxidation products (e.g., peroxidation products formed from unsaturated fatty acids). In the context of the present invention, the determination of whether a compound has antioxidant properties (and therefore is an antioxidant) may include, but is not limited to, ascertaining whether the compound inhibits activation of the fibrogenesis cascade in the liver; as described in the Experimental section, such inhibition may be represented by a decrease in MDA-adducts and stellate cell activation, and decreased expression of c-myb and collagen α1(I) mRNA in stellate cells. Examples of compounds with antioxidant properties include vitamin E, beta carotene, propyl gallate, ascorbyl palmitate, and sodium bisulfite. Antiox® (Mayrand Pharmaceuticals, Greensboro, N.C.) is an antioxidant product that is commercially available over-the-counter; it contains beta carotene, vitamin C, and vitamin E. It should be noted that compounds that are antioxidants may also have other pharmacological functions.

The term "therapeutic composition" refers to a composition that includes a compound in a pharmaceutically acceptable form that prevents and/or reduces hepatic fibrosis. Generally speaking, the therapeutic compositions of the present invention contain a compound with antioxidant properties. The characteristics of the form of the therapeutic composition will depend on a number of factors, including the mode of administration. For example, a composition for oral administration must be formulated such that the antioxidant compound is pharmacologically active following absorption from the gastrointestinal tract. The therapeutic composition may contain diluents, adjuvants and excipients, among other things.

The term "parenterally" refers to administration to a subject through some means other than through the gastrointestinal tract or the lungs. Common modes of parenteral administration include, but are not limited to, intravenous, intramuscular, and subcutaneous administration.

The terms "therapeutic amount," "effective amount," and the like refer to that amount of a compound or preparation that successfully prevents the symptoms of hepatic fibrosis and/or reduces the severity of symptoms. The effective amount of a therapeutic composition may depend on a number of factors, including the age, immune status, race, and sex of the subject and the severity of the fibrotic condition and other factors responsible for biologic variability.

The phrase "refractory to interferon" means that a treatment regimen involving the administration of interferon (e.g., interferon alpha) to a subject has had either no effect or a limited effect on the symptoms of hepatitis C. That is, interferon therapy may have alleviated some of the subject's symptoms, but it did not alleviate all of the symptoms associated with hepatitis C viral infection or disease. In certain, but not all, cases, further treatment with interferon is deemed to be medicinally unwarranted.

The term "vitamin E" is used synonymously with the term "d-α-tocopherol". Vitamin E activity is generally expressed in USP or International Units (IU), which are equivalent. One unit of vitamin E equals the biological activity of 1 mg of dl-α-tocopherol acetate, 1.12 mg of dl-α-tocopherol acid succinate, 910 μg of dl-α-tocopherol, 735 μg of d-α-tocopherol acetate, 830 μg of d-α-tocopherol acid succinate, and 670 μg of d-α-tocopherol.

DESCRIPTION OF THE INVENTION

Figure 1:
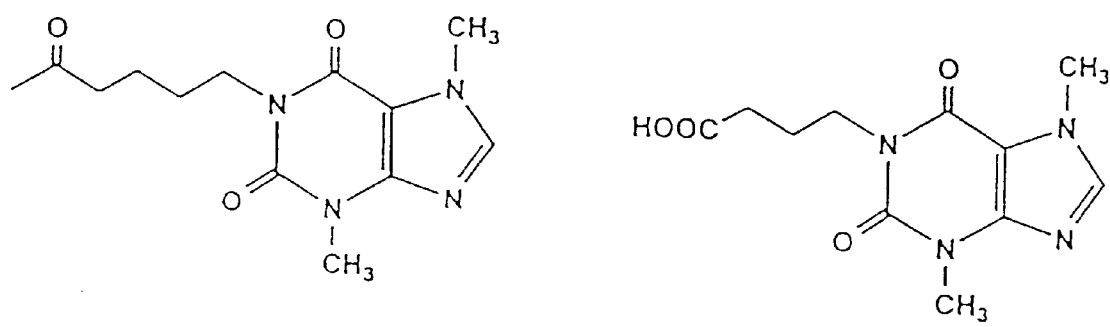
FIG. 1 depicts the chemical structures of pentoxifylline, 1-(5-oxohexyl)-3, 7-dimethyixanthine, and metabolite 5, an N-1 carboxypropyl derivative of pentoxifylline.

The present invention relates generally to the administration of antioxidants for the treatment and prevention of hepatic fibrosis, and more particularly to the administration of vitamin E and other pharmacologically active compounds for the treatment and prevention of viral hepatitis C.

The description of the invention is divided into the following sections: I) New Therapies for the Treatment of Chronic Hepatitis C, II) New Compounds for Treating Hepatic Fibrosis, and III) Formulation and Administration of Compounds.

I. NEW THERAPIES FOR THE TREATMENT OF CHRONIC HEPATITIS C

A. Hepatitis C and Fibrosis

In general, chronic hepatitis is characterized as an inflammatory liver disease continuing for at least six months without improvement. Chronic hepatitis C represents one form of chronic hepatitis. The prevalence of hepatitis C virus (HCV) infection in the general population exceeds 1% in the United States, Japan, China and Southeast Asia. Left unchecked, chronic hepatitis C can progress to cirrhosis and extensive necrosis of the liver.

Although chronic hepatitis C is often associated with deposition of collagen type I leading to hepatic fibrosis, the mechanisms of fibrogenesis remain unknown. Indeed, there is no established treatment for hepatic fibrogenesis related to the over-production of collagen type I. [See, e.g, Maher and McGuire, J. Clin. Invest. 86:1641-48 (1990); Chojkier *Pathogenesis of hepatic fibrosis. In Extracellular Matrix* (Marcel Dekker Inc., New York, N.Y.), pp. 541–57 (1993)]. The present inventors found that oxidative stress plays a major role in the activation of stellate cells in chronic hepatitis C. As described in detail in the Experimental section, lipid peroxidation (increased oxidative stress as indicated by the presence of malondialdehyde protein adducts) was found to be markedly increased in areas with active inflammation, and more conspicuously in stellate cells. The stellate cells that exhibit enhanced oxidative stress are activated and express collagen α1(I) mRNA as detected by in situ hybridization.

B. Vitamin E and Hepatitis C

The present inventors previously found that d-α-tocopherol (Vitamin E) injected into mice decreases collagen expression in the liver and tendons; however, it did not inhibit collagen expression by the skin or cultured smooth muscle cells. Water-soluble vitamin E failed to inhibit activation and collagen expression in cultured stellate cells. Other antioxidants that have demonstrated success in inhibiting activation and collagen production include BW-755c, probucol, and propyl gallate. [J. Clin. Invest. 87:2230-35 (1991)].

Based on the evidence supporting an oxidative stress pathway leading to active fibrogenesis in chronic hepatitis C and their prior in vitro studies, the inventors initiated a controlled study to determine the effectiveness of the antioxidant d-α-tocopherol. Specifically, human subjects with confirmed chronic hepatitis C who were refractory to interferon therapy were treated with high doses (1,200 IU/day) of d-α-tocopherol for 8 weeks. The treatment regimen prevented the fibrogenesis cascade characteristic of severe chronic hepatitis C (e.g., oxidative stress, induction of c-myb, activation of stellate cells, and collagen gene expression) without an effect on the inflammation associated with the disease. In addition, d-α-tocopherol treatment significantly decreased the carbonyl modifications of plasma proteins, a sensitive index of oxidative stress. This study is believed to be the first reported use of antioxidant therapy, and specifically treatment with vitamin E, for hepatitis C.

The present invention contemplates the administration of oral daily doses of vitamin E for the treatment of chronic hepatitis C ranging from 100 to 2000 IU (i.e., units), preferably from 800 to 1600 IU, and more preferably from 1000–1200 IU. Of course, the dose will depend on patient-specific variables such as the severity of the disease and the patient's age. Other dosing regimens are within the scope of the present invention, and other routes of administration (e.g., intramuscular) for vitamin E are also contemplated by the present invention.

In addition to their work with patients with chronic hepatitis C, the present inventors found increased oxidative stress in the livers and in proteins of certain patients with chronic hepatitis B with and without cirrhosis. In contrast to the findings relating to hepatitis C, hepatitis B virus-positive individuals with negligible hepatocellular inflammation exhibited no evidence of enhanced oxidative stress. A few studies have been performed to ascertain the effectiveness of antioxidant therapy in hepatitis B. For example, one study investigated the use of recombinant alpha 2-interferon with tocopherol administered rectally to children with viral hepatitis B. [Reizis et al., "Effectiveness Of Using Recombinant Interferon Alfa$_2$ (Reaferon) Combined With Antioxidants In Children With Acute Hepatitis B," Pediatriia 1:60–64 (1992)]. A second investigation examined the use of tocopherol acetate and splenin for the treatment of viral hepatitis B. Based on the results of this study, the researchers recommended the use of tocopherol acetate and splenin for hepatitis B treatment. [Frolov et al., "The Tocopherol Acetate And Splenin Correction Of The Immunological Disorders In Patients With Viral Hepatitis B," Vrach Delo 4:90–91 (1992)]. However, Frolov et al. did not indicate that the treatment regimen resulted in the reduction of the fibrotic symptoms associated with hepatitis B. Moreover, neither of these studies explored the treatment of hepatitis C with antioxidants.

C. Combination Therapy For Hepatitis C

The present invention also contemplates the co-administration of antioxidants such as vitamin E with other agents in order to treat chronic hepatitis C. To illustrate, two (or more) agents might be administered together in a manner similar to current treatment regimens for Mycobacterium tuberculosis. For example, vitamin E might be administered in conjunction with interferon alpha in a treatment regimen that allows lower doses of interferon alpha, with a concomitant reduction in its adverse effects.

Similarly, the present invention also contemplates the creation of novel dosage formulations containing both vitamin E and at least one other agent. For example, vitamin E might be stably combined with ursodeoxycholic acid (a bile acid) in a tablet or capsule form. Or, a composition comprising vitamin E and BHT might be formulated.

II. NEW COMPOUNDS FOR TREATING HEPATIC FIBROSIS

A. Metabolite 5 of Pentoxifylline

Based on in vivo experiments, the present inventors found that pentoxifylline and metabolite 5, a N-1 carboxypropyl derivative, inhibit stellate cell activation, thereby preventing liver fibrosis. Pentoxifylline [1-(5-oxohexyl)-3, 7-dimethylxanthine; Trental® (Hoechst)] is a tri-substituted xanthine derivative that has been used most frequently in the management of peripheral vascular disease and cerebrovascular disease and is thought to be extensively metabolized by erythrocytes and the liver. Metabolite 5 [1-(3-carboxypropyl)-3, 7-dimethylxanthine] is one of two primary metabolites formed during the metabolism of pentoxifylline, and it generally has a plasma concentration five times greater than pentoxifylline. [See generally, *AHFS Drug Information*, Gerald K. McKevoy, ed., pp. 996–1000 (1995)]. The molecular structures of pentoxifylline and metabolite 5 are depicted in FIG. 1.

Although pentoxifylline, a non-specific inhibitor of cyclic nucleotide phosphodiesterases [Nicholson et al., Trends Pharmacol. Sci. 12:19–277 (1991)], inhibits collagen gene expression in dermal fibroblasts [Berman et al., J. Invest. Dermatology 98:706–712 (1992)], the mechanisms responsible for this effect are unknown. In a previous study, it was reported that the administration of pentoxifylline prevented hepatic fibrosis in an animal model involving phosphorus-induced hepatocellular necrosis. [Peterson, Hepatology 17:486–93 (1992)]. The results suggested that pentoxifylline is protective whether administered simultaneously or after the onset of fibrosis. However the study did not determine whether the prevention of hepatic fibrosis by pentoxifylline was due to prevention of the injury or modulation of fibrogenesis. Moreover, the use of metabolite 5 of pentoxifylline to prevent liver fibrosis was not reported by Peterson and is not believed to have been reported previously.

As described in detail in the Experimental section, the present inventors found that both pentoxifylline and metabolite 5 prevented stellate cell activation in vivo in hepatic injury induced by $CCl_4$. Though a precise understanding of the molecular basis for the prevention of stellate cell activation of pentoxifylline and metabolite 5 is not necessary to practice the present invention successfully, the experimental results indicate that the prevention is mediated, at least in part, through inhibition of NFkB activity and c-myb expression. NFkB is a protein specific to B cells which binds to a specific DNA sequence within the immunoglobulin light chain kappa locus enhancer region in mice and humans. The protein plays important roles in the regulation of cell growth and function, and oxidative stress increases NFkB activity.

It is believed that stellate cell activation is a critical step in hepatic fibrosis. Because metabolite 5, which lacks phosphodiesterase inhibitory activity, was shown to prevent hepatic stellate cell activation and proliferation (see Example 1), the present invention contemplates using the compound in the treatment of hepatic fibrosis. Similarly, metabolite 5 may also be effective at preventing and treating hepatic disorders associated with fibrosis.

The present invention contemplates the administration of oral daily doses of metabolite 5 ranging from 200 to 1500 mg, and more preferably from 400–1200 mg. The dose will depend on patient-specific variables such as the severity of the disease and the patient's age. Other dosing regimens are within the scope of the present invention, and other routes of administration are also contemplated by the present invention.

B. Butylated Hydroxytoluene And Other Antioxidants

The present inventors have also tested other antioxidants that successfully prevented liver fibrosis by the inhibition of stellate cell activation. As set forth in the Experimental section, the present inventors have also shown that stellate cell activation initiated by collagen type I matrix and TGFα is inhibited by butylated hydroxytoluene (BHT). Quiescent hepatic stellate cells produce low levels of collagen type I, whereas activated (myofibroblastic) hepatic stellate cells (lipocytes) exhibit high levels of collagen α1 (I) and smooth muscle actin gene expression. BHT inhibition prevents collagen production and thus prevents liver fibrogenesis. BHT [2,6-Bis(1,1-dimethylethyl)-4-methylphenol or 2,6,Di-tert-butyl-4-methylphenol] is an antioxidant sometimes used in conjunction with food products and animal feed. This compound is insoluble in water, but soluble in alcohols like ethanol and isopropanol.

The finding that BHT inhibited stellate cell activation was surprising and unexpected because it conflicted with previous findings. Specifically, McCormick et al. [Toxicol. Appl. Pharmacol. 90(1):1–9 (1987); and Cancer Res. 46(10):5264–69 (1986)] examined, among other things, the induction of hepatic fibrosis resulting from interaction of the vitamin A ester retinyl acetate and BHT. These researchers found that BHT used in combination with retinyl acetate potentiated hepatic fibrosis, rather than prevented it.

Based on the experimental results described below, the present invention contemplates the use of BHT in the treatment of hepatic fibrosis. The present invention contemplates that BHT will be administered orally to subjects. Previous investigations have examined dietary administration of 5000 mg/kg BHT to rats. [McCormick et al. Toxicol. Appl. Pharmacol. 90(1):1–9 (1987); and Cancer Res. 46(10):5264–69 (1986)]. Though not limited to any particular dosing range, the present invention contemplates oral daily BHT doses ranging from 500 mg/kg to 7000 mg/kg (diet). Of course, the dose will depend on patient-specific variables such as the severity of the disease and the patient's age, and other dosing regimens, including other routes of administration, are within the scope of the present invention.

III. FORMULATIONS AND ADMINISTRATION OF COMPOUNDS

As alluded to above, the present invention contemplates using therapeutic compositions of antioxidant agents, including metabolite 5 of pentoxifylline, BHT, and vitamin E, for the treatment and prevention of viral hepatitis C and other chronic liver diseases. It is not intended that the present invention be limited by the particular nature of the therapeutic preparation. For example, such compositions can be provided together with physiologically tolerable liquid (e.g., saline), gel or solid carriers or vehicles, diluents, adjuvants and excipients, such as pharmaceutical grades of mannitol, lactose, starch, magnesium stearate, sodium saccharin, cellulose, magnesium carbonate, and the like. These compositions typically contain 1%–95% of active ingredient, preferably 2%–70%. In addition, the compositions may contain minor amounts of auxiliary substances such as wetting or emulsifying agents, stabilizing or pH buffering agents or preservatives if desired. The therapeutic compositions contemplated by the present invention are physiological tolerable and compatible.

These therapeutic preparations can be administered to humans in a manner similar to other therapeutic agents. In general, the dosage required for therapeutic efficacy will vary according to the type of use and mode of administration, as well as the particularized requirements of individual hosts. The present invention also contemplates the administration of the therapeutic compositions to other animals for veterinary use, such as with domestic animals.

The preferred mode of administration of these preparations depends on several factors, including the stability of the preparation, the bioavailability of the compound following different routes of administration, and the frequency of dosing. Vitamin E is preferably administered orally. A number of oral preparations are commercially available, including tablets, capsules, drops and chewable tablets. When oral administration is not feasible or when malabsorption is suspected, vitamin E may be administered parenterally as a component of a multivitamin injection. Likewise, oral administration is a preferred route of administration for metabolite 5 and BHT.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); mM (millimolar); $\mu$M (micromolar); N (Normal); mol (moles); mmol (millimoles); $\mu$mol (micromoles); nmol (nanomoles); g (grams); mg (milligrams); $\mu$g (micrograms); Kg (kilograms); L (liters); mL (milliliters); $\mu$L (microliters); cm (centimeters); mm (millimeters); $\mu$m (micrometers); nm (nanometers); h and hr (hours); min. (minutes) s and sec. (seconds); °C. (degrees Centigrade); v/v (volume/volume); w/v (weight/volume) $\mu$Ci (microcuries); FDA (United States Food and Drug Administration); DME (Dulbecco's Modified Eagles Medium); LDL (low-density lipoprotein); DMF (N,N-dimethylformamide); $\alpha$-SMA ($\alpha$-smooth muscle actin); MDA (malondialdehyde); 4-HNE (4-hydroxynonenal); PBS (phosphate buffered saline); FBS (fetal bovine serum); PDGF (platelet-derived growth factor), EGF (epidermal growth factor); FGF (fibroblast growth factor); HPLC (high pressure liquid chromatography); PCNA (proliferating cell nuclear antigen); CREB (cAMP responsive element binding protein); NMR (Nuclear Magnetic Resonance); $K_2CO_3$ (potassium carbonate); $NaHCO_3$ (sodium bicarbonate); $MgCl_2$ (magnesium chloride); NaOH (sodium hydroxide); $FeSO_4$ (ferrous sulfate); $MgSO_4$ (magnesium sulfate); SD or S.D. (standard deviation); SEM (standard error of the mean); Accurate Chemical & Scientific Corp. (Westbury, N.Y.); Amersham (Arlington Heights, Ill.); Charles River Breeding Labs (Wilmington, Mass.); Clonetics (Clonetics Corp., San Diego, Calif.); Collaborative Bio-medical Products (Bedford, Mass.); DuPont (DuPont Co., Wilmington, Del.); Hitachi (Hitachi Scientific Instruments, Mountain View, Calif.); Hoechst (Santa Cruz Biotechnology, Santa Cruz, Calif.); Sigma (Sigma Chemical Company, St. Louis, Mo.); Upstate Biotechnology (Lake Placid, N.Y.); Vector Laboratories (Burlingame, Calif.).

Unless otherwise indicated, results are expressed as the mean (±S.D.) of experiments performed at least in triplicate. The Student-t was used to evaluate the differences of the means between groups, with a P value of less than 0.05 considered significant.

EXAMPLE 1

Inhibition Of Stellate Cell Activation With Pentoxifylline and Metabolite 5

This example evaluates the effect of pentoxifylline and its metabolite 5 on stellate cell activation in vivo. Treatment with pentoxifylline or metabolite 5 prevented stellate cell activation, and the molecular abnormalities characteristic of stellate cell activation, induced by $CCl_4$.

A. Methodology

Animals

At least four Sprague-Dawley (Charles River Breeding Labs) male rats (50 to 60 g) were assigned to each of four testing groups (designated as "$CCl_4$", "pentoxifylline", "metabolite 5", and "control"). Each rat received a single intraperitoneal injection of $CCl_4$ in mineral oil (1:3; v/v) at a dose of 2 mL/kg body weight ($CCl_4$, pentoxifylline, and metabolite 5 groups), or mineral oil only (control group). In addition, animals received intraperitoneal injections (100 $\mu$L) of saline (control and $CCl_4$ groups), 200 mg/kg pentoxifylline (pentoxifylline group), or 200 mg/kg of the ester prodrug of pentoxifylline metabolite 5 (metabolite 5 group) at the following times with respect to mineral oil or $CCl_4$ administration: −4 h, +8 h, +20 h, +32 h, and +44 h. The last injection (at+44 h) included 30 $\mu$Ci of 6-[$^3$H] thymidine (DuPont). As described further below, the dose of pentoxifylline used was not toxic to the animals, judging by their normal behavior, lack of hepatotoxicity, and preservation of c-AMP mediated phosphorylation of stellate cells.

Forty-eight hours after the $CCl_4$ or mineral oil injection (and 4 hours after the [$^3$H] thymidine injection), the rats were sacrificed. Thereafter, liver tissues were promptly removed, and a piece was fixed in 10% formaldehyde and embedded in paraffin for immunohistochemical staining.

Cell Isolation

Hepatic stellate cells were prepared from rats by in situ perfusion of the liver and single-step density Nycodenz® gradient (Accurate Chemical & Scientific Corp.). [See Bedossa el al., Hepatology 19(5):1262–71 (1994); Brenner et al., Mol. Biol. Med. 7:105–15 (1990); Schafer et al., Hepatology 7(4):680–87 (1987)]. The cells were mixed with 9.5 mL Hank's buffer containing 3 g/L BSA and 8 mL of 28.7% (w/v) Nycodenz® in sodium-free Hank's buffer. The gradient was generated by placing 6 mL of the Hank's/BSA solution on top of the liver cell mixture in a 50 mL centrifugation tube. After centrifugation (1000 g, 4° C., 20 min) the cells were aspirated from above the interface, washed twice in serum-free DME glucose medium, and collected.

Stellate cells were identified by their typical autofluorescence at 328 nm excitation wavelength, staining of lipid droplets by oil red, and immunohistochemistry with a monoclonal antibody against desmin. [Bedossa et al., Hepatology 19(5):1262–71 (1994)]. Detection of $\alpha$-SMA, malondialdehyde-protein adducts, and CREB-PSer 133 in stellate cells extracts was performed by Western blot [Buck et al., EMBO J. 13:851–60 (1994)], and using antibodies directed against $\alpha$-SMA (Vector Laboratories), malondialdehyde-lysine epitopes as described below [Trautwein et al., J. Clin. Invest. 93:2554–61 (1990)], or CREB-PSer 133 (Upstate Biotechnology).

Nuclear Extract Preparation

Nuclei were prepared by a modification of the procedure described previously, e.g., by Buck et al., EMBO J. 13:851–60 (1994). Briefly, cells were homogenized in 1 mL of 5% citric acid, 0.5% NP-40, 10 mM sodium fluoride and 10 mM sodium pyrophosphate with a glass Dounce homogenizer with a loose fitting pestle. The homogenized cells were placed above a cushion consisting of 30% sucrose and 1% citric acid. The nuclei were precipitated by a 4,000 g centrifugation at 4° C. for 30 min. and frozen at −70° C. DNA was isolated, extracted and counted for [$^3$H] thymidine incorporation.

Gel retardation analysis of protein-DNA complexes were performed with an oligonucleotide of the putative DNA binding site. The sense oligonucleotides were as follows: NFkB (5' GGG GAC TTT CCC 3') (SEQ ID NO:1) and α-smooth muscle actin E box (5' GAT CAT AAG CAG CTG AAC TGC C 3') (SEQ ID NO:2). Antibodies directed against c-myb and NFKB365 were obtained from Santa Cruz Biotechnology. [Buck et al., EMBO J. 13:851–60 (1994)].

Immunohistochemistry

Liver tissue was immunostained with antisera, specific for malondialdehyde-lysine adducts, raised against malondialdehyde-lysine adducts as described by Houglum et al., J Clin Invest 96:2269–76 (1995). Briefly, guinea pig LDL was isolated and modified with MDA, and the homologous modified LDL was used to immunize guinea pigs. The resultant antisera were specific for the adducts to LDL and did not react with native LDL.

A phase-contrast microscope was utilized for hematoxylin/eosin staining and immunohistochemistry with alkaline phosphatase secondary antibodies (Vector Laboratories). Cytochromes utilized were alkaline phosphatase with fast green as counterstain (Sigma Chemical Co.). Negative control samples were processed in parallel under the same conditions, but with omission of the primary antibody.

Synthesis of Pentoxifylline Metabolite 5

The metabolite 5 of pentoxifylline (1-[3 carboxypropyl]-3,7 dimethylxanthine) and its ethyl ester were synthesized as described by Cottam et al, J. Med. Chem. in press (1995). Briefly, theobromine (2 mmol) was combined with anhydrous $K_2CO_3$ (2.5 mmol) and dry DMF (15 mL) and the mixture was brought to 75° C. The alkyl halide (2.5 mmol) was added and the mixture was stirred at 75° C. for 18 h. The reaction mixture was cooled, poured into water (125 mL) and extracted with ethyl acetate (2×75 mL).

The organic layer was dried over magnesium sulfate and evaporated to yield a white solid which was triturated with ethyl ether. The resulting solid, analytically pure, was further purified by crystallization. H NMR spectrum, elemental analyses and exact mass data (not shown) were consistent with the assigned structure for metabolite 5 shown in FIG. 1.

B. Inhibition of Hepatic Stellate Cell Proliferation And Activation

Stellate cell proliferation was assessed by the incorporation of [$^3$H] thymidine. Stellate cell activation was evaluated by the expression of a-smooth muscle actin (α-SMA). [See Rockey et al., J. Submicrosc. Cytol. 24:193–203 (1992)]. For example, fixed specimens may be incubated overnight with anti-smooth muscle actin (e.g., 1:200) as the primary antibody, and then washed and incubated with biotinylated second antibody (e.g., anti-rabbit IgG, Vector Laboratories); after washing, the specimens may be incubated with streptavidin-linked Texas Red (Amersham) for 30 minutes, washed a second time, and mounted for photomicrography.

The specific activity of stellate cell DNA, an index of S-phase labeling, was determined from at least four rats in each experimental group after 4 hours of labeling with [$^3$H] thymidine at 1 PM; labeling at that time helped to avoid potential variability related to the circadian rhythm. The dose of [$^3$H] thymidine (corrected for body weight) was given intraperitoneally in order to facilitate hepatic bioavailability.

Figure 2A:
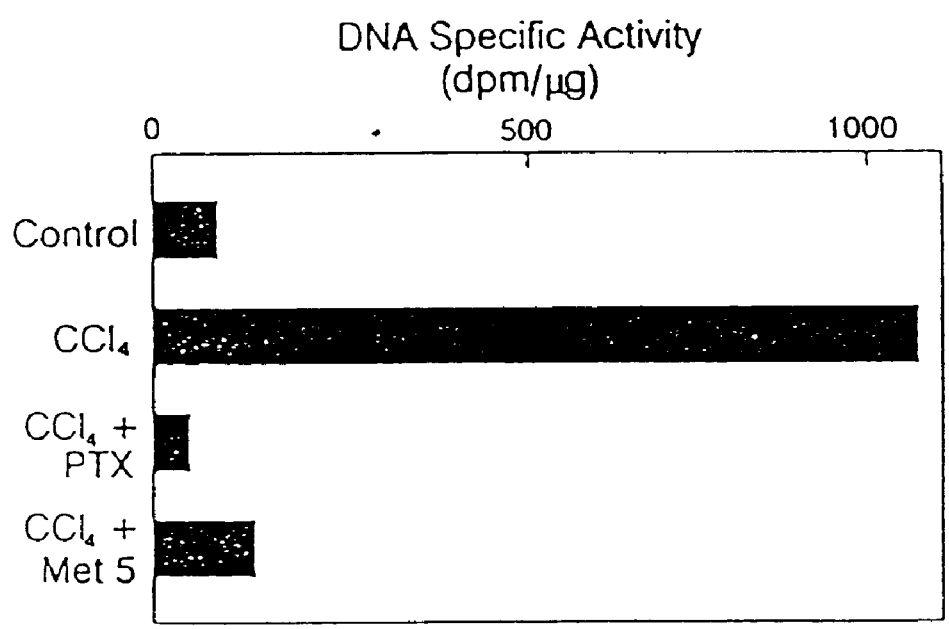
FIG. 2A graphically depicts the effect of pentoxifylline and metabolite 5 on stellate cell proliferation as measured by DNA specific activity.

The data presented in FIG. 2A illustrate that pentoxifylline and metabolite 5 inhibited stellate cell proliferation and activation. As depicted in FIG. 2A, the stellate cells DNA's [$^3$H] thymidine specific activity increased>10-fold 48 hours after the administration of $CCl_4$. Pentoxifylline treatment abolished the proliferation of stellate cells in the $CCl_4$-treated animals, suggesting an inhibitory effect of pentoxifylline on stellate cell activation. A similar effect is shown for metabolite 5. [$P<0.05$ for $CCl_4$ compared to all other groups; SEM<20% of the mean for all treatment conditions].

Figure 2B:
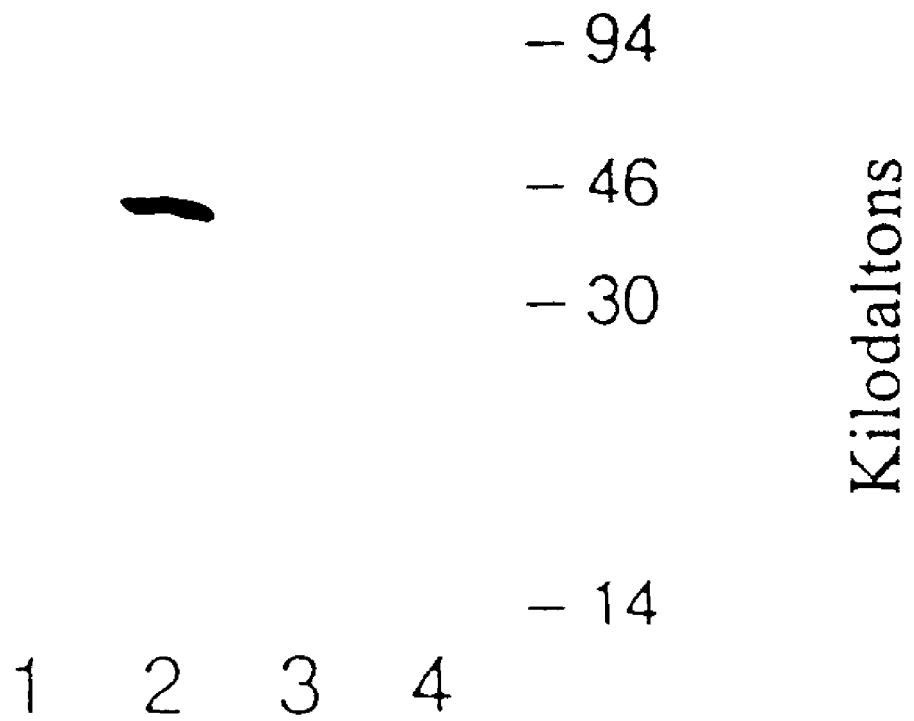
FIG. 2B depicts the effect of pentoxifylline and metabolite 5 on α-smooth muscle actin (α-SMA) expression, a measure of stellate cell activation, in hepatic stellate cells by Western blot.

The data presented in FIG. 2B illustrate that pentoxifylline and metabolite 5 inhibited stellate cell activation. More specifically, FIG. 2B depicts the effect of pentoxifylline and metabolite 5 on α-SMA expression in hepatic stellate cells, a measure of stellate cell activation, by Western blot. Referring to FIG. 2B, lane 1=control, lane 2=$CCl_4$ administration, lane 3=$CCl_4$/pentoxifylline co-administration, and lane 4=$CCl_4$/metabolite 5 co-administration; molecular markers (kilodaltons) are shown on the right margin. Hepatic stellate cells of control animals (lane 1) were activated by treatment with $CCl_4$, as indicated by the increased expression of α-SMA on Western blots of freshly isolated stellate cells (lane 2). Treatment with pentoxifylline and metabolite 5 prevented the activation of stellate cells induced by $CCl_4$, as indicated by the absence of increased expression of α-SMA (lanes 3 and 4, respectively).

C. Effect Of Pentoxifylline On Hepatocellular Injury and Lipid Peroxidation

In order to ascertain whether or not the prevention of activation observed with pentoxifylline resulted from interfering with the hepatocellular injury induced by $CCl_4$, the degree of hepatocellular injury and lipid peroxidation were determined in those animals. As indicated by liver staining with hematoxylin/eosin (not shown) and by the release of liver enzymes into the blood (serum alanine aminotransferase: 125±10 vs 135±4 IU/mL, P not significant), the degree of hepatocellular necrosis was similar in the $CCl_4$ and $CCl_4$/pentoxifylline groups. Moreover, the degree of hepatic lipid peroxidation was comparable in both the $CCl_4$ and $CCl_4$/pentoxifylline groups. As set forth above, protein adducts with malondialdehyde were detected using specific antibodies against malondialdehyde-lysine epitopes. No adducts were detected in the livers of control animals, whereas enhanced lipid peroxidation was comparable at 48 hours in zones 2 and 3 of the hepatic acini in animals treated with $CCl_4$ alone or with $CCl_4$/pentoxifylline (not shown).

Similar to pentoxifylline, metabolite 5 did not affect the induction by $CCl_4$ of either hepatocellular necrosis (serum alanine aminotransferase: 115±5 vs 125±10 IU/mL; P not significant), or malondialdehyde-protein adducts in hepatic tissue (data not shown). Since the degree of hepatic cellular injury and lipid peroxidation was comparable in $CCl_4$-treated animals whether or not they were treated with pentoxifylline or metabolite 5, neither pentoxifylline nor metabolite 5 affected the hepatic oxidative stress cascade characteristically initiated by $CCl_4$. [See Bedossa et al., Hepatology 19(5):1262–71 (1994)]. This is in contrast with results obtained using prostaglandin $E_2$ and d-α-tocopherol, which ameliorate hepatocellular necrosis in nutritional- or $CCl_4$-induced injury. [Ruwart et al., Hepatology 8:61–64 (1988); Yao et al., Am. J. Physio. 267:476–84 (1994)].

D. Role of NFkB in Stellate Cell Activation

Figure 3A:
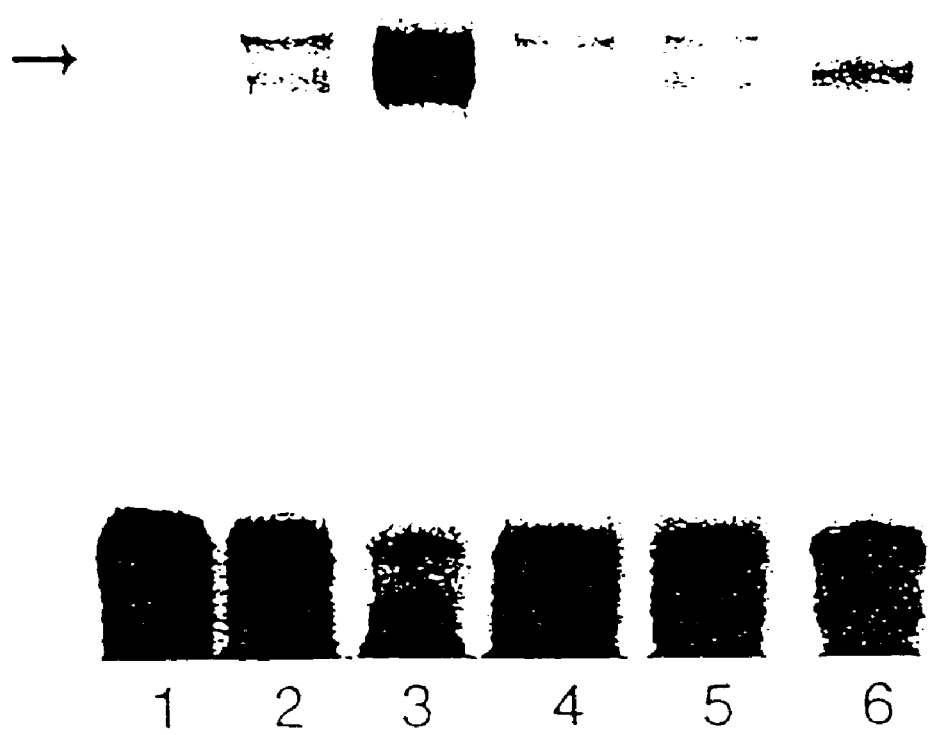
FIG. 3A depicts DNA-protein complexes resolved by gel electrophoresis for representative samples of control (lane 2), $CCl_4$ (lane 3), $CCl_4$/pentoxifylline (lane 4); $CCl_4$/metabolite 5 (lane 5); and $CCl_4$+NFkB oligonucleotide (lane 6).
Figure 3B:
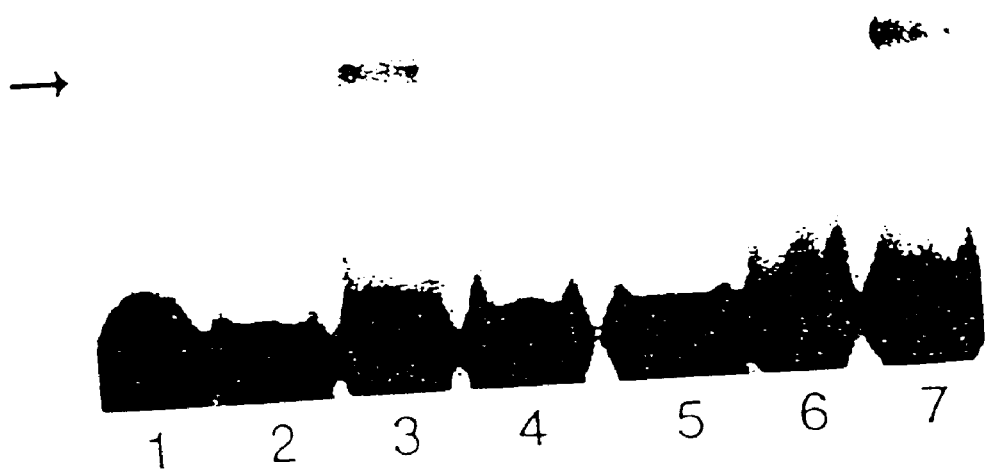
FIG. 3B depicts DNA-protein complexes resolved by gel electrophoresis for representative samples of control (lane 2), $CCl_4$ (lane 3), $CCl_4$/pentoxifylline (lane 4); $CCl_4$/metabolite 5 (lane 5), $CCl_4$+c-myb antibodies (lane 6), and $CCl_4$ +NFkB oligonucleotide (lane 7).

Because oxidative stress increases NFkB activity, and NFkB plays important roles in the regulation of cell growth and function, the potential role of NFkB regulation in stellate cell activation in animals treated with $CCl_4$ was analyzed. Stellate cell activation was associated with the nuclear translocation and activation of NFkB, as detected by gel shift analysis. FIGS. 3A–B illustrate through mobility shift analysis of stellate cell nuclear extracts that pentoxifylline and metabolite 5 block the increase in NFkB and α-SMA binding activities of activated stellate cells. For these analyses, equal amounts of nuclear protein were incubated with 1 ng of $^{32}$P-labeled-NFkB (FIG. 3A) or $^{32}$P-labeled-α-SMA-E box (FIG. 3B) oligonucleotides. The DNA-protein complexes were resolved by electrophoresis on a 6% nondenaturing polyacrylamide gel, the position of the bound DNA being indicated by arrows in FIGS. 3A–B. As described further below, some samples were incubated with specific antibodies or unlabeled oligonucleotide.

More specifically, FIG. 3A depicts DNA-protein complexes resolved by gel electrophoresis for representative samples of control (lane 2), $CCl_4$ (lane 3), $CCl_4$/pentoxifylline (lane 4); $CCl_4$/metabolite 5 (lane 5); and $CCl_4$ +NFkB oligonucleotide (lane 6). On lane 1, the $^{32}$P-labeled-NFkB probe was processed without nuclear extracts. As the results in FIG. 3A indicate, the binding of stellate cell nuclear extracts to a NFkB cognate oligonucleotide was low in quiescent cells from control animals (lane 2), but increased significantly following stellate cell activation after treatment with $CCl_4$ (lane 3). The complex of $^{32}$P-labeled NFkB oligonucleotides and nuclear extracts from activated stellate cells was competed by a NFkB cognate oligonucleotide (lane 6). Pentoxifylline and metabolite 5 treatment prevented NFkB nuclear activity induced by $CCl_4$ (lanes 4 and 5, respectively).

FIG. 3B depicts DNA-protein complexes resolved by gel electrophoresis for representative samples of control (lane 2), $CCl_4$ (lane 3), $CCl_4$/pentoxifylline (lane 4); $CCl_4$/metabolite 5 (lane 5), $CCl_4$+c-myb antibodies (lane 6), and $CCl_4$+NFkB oligonucleotide (lane 7). On lane 1, the $^{32}$P-labeled-α-SMA-E box probe was processed without nuclear extracts. Because c-myb is an important inducer of proliferation in cultured hematopoletic, smooth muscle and stellate cells, whether c-myb expression plays a role in the activation of stellate cells in vivo was tested. The critical promoter E box of the α-SMA gene formed complexes with nuclear extracts from activated stellate cells from $CCl_4$ treated animals (lane 3), but not with nuclear extracts of quiescent stellate cells from control animals (lane 2). As indicated by lanes 4 and 5, treatment of $CCl_4$ animals with pentoxifylline and metabolite 5, respectively, prevented the formation of a complex between the α-SMA-E box and stellate cell nuclear extracts (an essential step in the activation of the α-SMA gene). The protein-DNA complexes were disrupted by monoclonal c-myb antibodies (lane 6) but not by a NFkB cognate oligonucleotide (lane 7). In addition, preimmune serum did not affect the protein-DNA complexes (not shown).

Though an understanding of the molecular basis for stellate cell activation is not required in order to practice the present invention, these results suggest a critical role of NFkB and c-myb on stellate cell activation in vivo, given that during stellate cell activation the nuclear activities of NFkB and c-myb are increased, and that these molecular changes and stellate cell activation are both blocked by pentoxifylline and its metabolite 5. Moreover, the determination in activated stellate cells from $CCl_4$-treated animals that c-myb contributes substantially to the nuclear binding activities to the key E box within the promoter of the α-SMA gene suggests that c-myb is the molecular mediator of oxidative stress on stellate cell activation, and that it binds to the critical E box of the α-SMA gene, the expression of which is intrinsic to the activated phenotype of stellate cells.

E. Biological Activities and Phosphodiesterase Activates Of Pentoxifylline And Metabolite 5

Figure 4A:
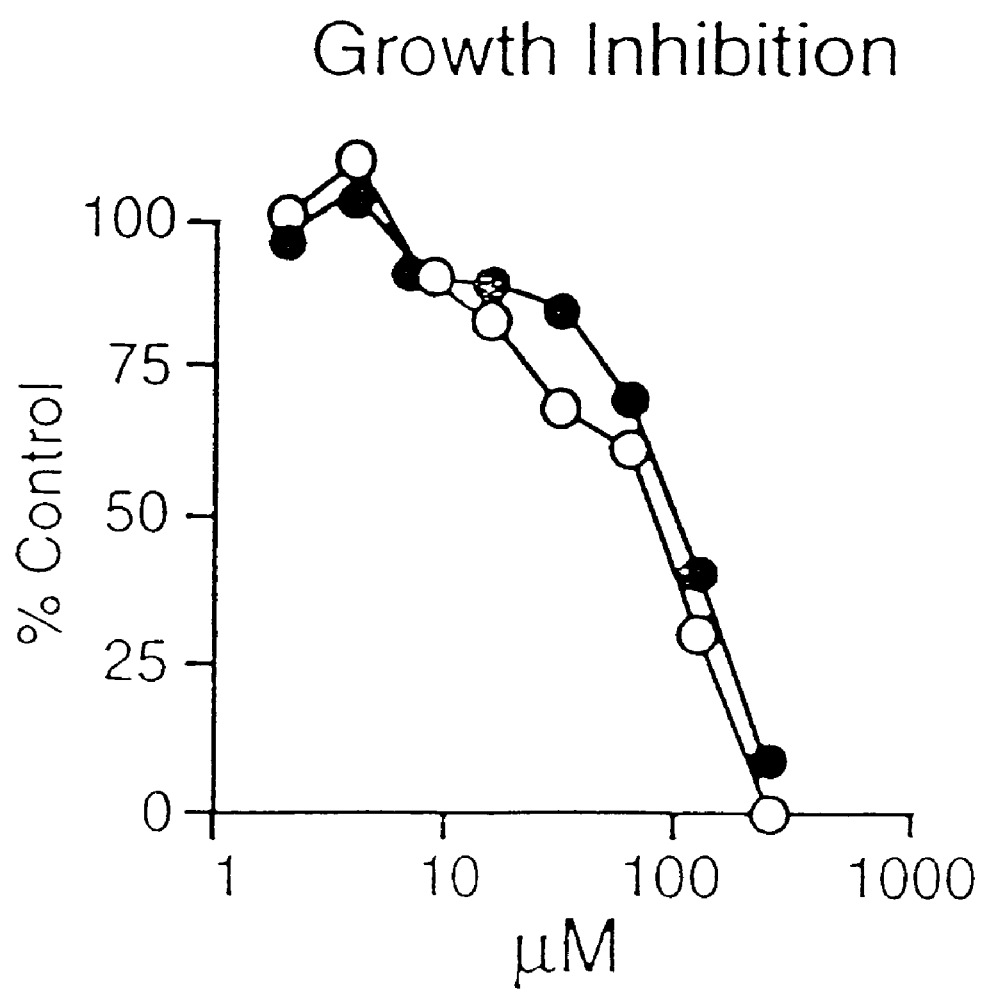
FIG. 4A graphically illustrates that both pentoxifylline (o-o) and metabolite 5 (●-●) block fibroblast growth in logarithmic phase.

The biological activities of pentoxifylline and metabolite 5 were further studied by measuring their effects on the stimulation of fibroblast proliferation. For this study, 3T3 NIH fibroblasts were cultured in the presence or absence of pentoxifylline or metabolite 5. FIG. 4A graphically illustrates that both pentoxifylline (○-○) and metabolite 5 (●-●) block fibroblast growth in logarithmic phase. In addition, both pentoxifylline and metabolite 5 blocked fibroblast growth induced by the cytokines PDGF, EGF and FGF (data not shown).

Next, pentoxifylline and metabolite 5 were evaluated to determine whether they inhibit cAMP phosphodiesterase activity in hepatic stellate cells in vivo leading to an increase in protein kinase A-mediate phosphorylation. Because this signal transduction pathway triggers site-specific phosphorylation of the nuclear transcription factor CREB (cAMP responsive element binding protein) on Serine 133 [Yamamoto et al., Nature 334:494–98 (1988)], the induction of CREB phosphorylation at Ser 133 was analyzed in nuclear extracts from freshly isolated stellate cells using an antibody against the activated, phosphorylated form of CREB [Ginty et al., Science 260:238–42 (1993)].

Figure 4B:
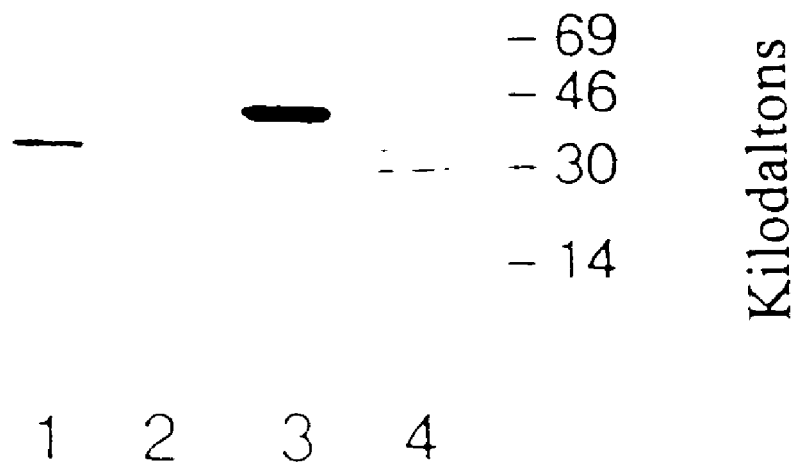
FIG. 4B is a Western blot indicating the results of phosphorylation of cAMP responsive element binding protein (CREB) at Serine 133 in stellate cell nuclear extracts with control (lane 1), $CCl_4$ (lane 2), $CCl_4$/pentoxifylline (lane 3), and $CCl_4$/metabolite 5 (lane 4) animals.

FIG. 4B is a Western blot indicating the results of phosphorylation of CREB at Serine 133 in stellate cell nuclear extracts with control (lane 1), $CCl_4$ (lane 2), $CCl_4$/pentoxifylline (lane 3), and $CCl_4$/metabolite 5 (lane 4) animals. As shown in FIG. 4B, treatment with pentoxifylline markedly increased the expression of CREB-PSer133 (43 kd) (lane 3), which was not detected in stellate cells from control (lane 1), $CCl_4$ (lane 2), or $CCl_4$/metabolite 5 (lane 4) groups. Molecular markers (kilodaltons) are shown on the right margin of FIG. 4B. In addition to recognizing CREB, anti-CREB-PSer133 detected two other proteins. These are most likely members of the CREB-ATF family, ATF-1 and CREM, that have phosphoacceptor sequences similar to that of CREB-PSer133 [Ginty et al., Science 260:238–42 (1993)]. Nuclear extracts of stellate cells isolated from control (lane 1) and $CCl_4$/metabolite 5 (lane 4) animals contain small amounts of phosphorylated ATF-1 (38 kd), and CREM (30 kd), but not CREB-PSer 133. Neither CREB PSer133 nor phosphorylated members of the CREB-ATF family were detected in stellate cell nuclear extracts from $CCl_4$-treated animals (lane 2).

The results presented in this example indicate that both pentoxifylline and metabolite 5 prevented stellate cell activation and proliferation and that cyclic nucleotide phosphodiesterase inhibitory activity is not indispensable to block stellate cell activation or proliferation. Thus, both agents are effective in preventing hepatic fibrosis and may be effective in the treatment and prevention of those hepatic disorders that have a fibrotic component.

EXAMPLE 2

Inhibition Of Stellate Cell Activation With BHT And Vitamin E

This example evaluates the effect of butylated hydroxytoluene (BHT) and vitamin E on stellate cell activation in vivo. As described below, stellate cell activation by collagen type I matrix and TGFα was blocked by BHT and vitamin E.

A. Methodology

Cell Cultures

Stellate cells were prepared from male Sprague-Dawley (400–500 grams) rats (Charles River Breeding Labs) by in situ perfusion of the liver and single-step density Nycodenz® gradient (Accurate Chemical & Scientific Corp.). [See Bedossa et al., Hepatology 19(5):1262–71 (1994); Brenner et al., Mol. Biol. Med. 7:105–15 (1990)]. The cells were mixed with 9.5 mL Hank's buffer containing 3 g/L BSA and 8 mL of 28.7% (w/v) Nycodenz® in sodium-free Hank's buffer. The gradient was generated by placing 6 mL of the Hank's/BSA solution on top of the liver cell mixture in a 50 mL centrifugation tube. After centrifugation (1000 g, 4° C., 20 min) the cells were aspirated from above the interface and washed twice in serum-free DME regular glucose medium.

Thereafter, the cells were cultured under an atmosphere of 5% $CO_2$, 95% air in tissue culture dishes using DME medium containing penicillin G 100 units/mL, streptomycin sulfate 100 µg/mL and 10% fetal calf serum. For TGFα-induced stellate cell activation, cells were cultured on plastic in serum-free defined media (Fibroblast basal medium with Insulin, Clonetics). Fibroblast basal medium is similar to F12 medium, but contains folinic acid, Hepes buffer with NaOH, $MgSO_4$, and adenine instead of folic acid, $NaHCO_3$, $MgCl_2$ and hypoxanthine. Cells were plated on 60-mm dishes coated with collagen type 1, EHS matrix (Matrigel; Collaborative Bio-medical Products) or plastic (according to the experimental design), for the initial seeding of fat-storing cells at a density of 2–3×106. Matrigel's major components are laminim, collagen IV, proteoglycans, entactin and nidogen; it also contains TGFβ, fibroblast growth factor, and tissue plasminogen activator.

Treatments were started 18 h after hepatic stellate cell isolation, and continued for an additional 120 h for cells cultured on plastic (with serum), EHS or collagen 1 matrices, and for an additional 60 h for cells cultured in serum-free defined media. Medium was changed every 24 h for all conditions. The sequences of c-myb oligonucleotide phosphorothioate were: sense (5' GCC CGG AGA CCC CGA CAC 3') (SEQ ID NO:3) and antisense (5' GTG TCG GGG TCT CCG GGC 3') (SEQ ID NO:4). Stellate cells were identified by their typical autofluorescence at 328 nm excitation wavelength, staining of lipid droplets by oil red, and immunohistochemistry with a monoclonal antibody against desmin. [Bedossa et al., Hepatology 19(5):1262–71 (1994)].

Nuclear Extract Preparation

Nuclei were prepared by a modification of the procedure described previously, e.g., by Buck et al., EMBO J. 13:851–60 (1994). Briefly, cells were homogenized in 1 mL of 5% citric acid, 0.5% NP-40, 10 mM sodium fluoride and 10 mM sodium pyrophosphate with a glass Dounce homogenizer with a loose fitting pestle. The homogenized cells were placed above a cushion consisting of 30% sucrose and 1% citric acid. The nuclei were precipitated by a 4,000 g centrifugation at 4° C. for 30 mm. and frozen at −70° C.

Gel retardation analysis of protein-DNA complexes were performed with an oligonucleotide of the putative DNA binding site. The sense oligonucleotides were as set forth in the preceding example, i.e., NFkB (5' GGG GAC TTT CCC 3') (SEQ ID NO:1) and α-smooth muscle actin E box (5' GAT CAT AAG CAG CTG AAC TGC C 3') (SEQ ID NO:2).

Animals

C57BL/6 mice (20–25 g) each received a single intraperitoneal injection of $CCl_4$ in mineral oil (1:3, v/v) at a dose of 2 mL/kg body weight, or mineral oil only (control). Forty-eight hours after the $CCl_4$ or mineral oil injection, the rats were sacrificed. After 48 h, animals were sacrificed and liver tissues were promptly removed, fixed in 10% formaldehyde and embedded in paraffin for immunohistochemical staining.

Immunohistochemistry

Cells, fixed with acetone:methanol (50:50) at −20° C. for 20 min., and liver tissue were immunostained as described, e.g., by Buck et al., EMBO J. 13:851–60 (1994). Antibodies directed against c-myb, NFkB65, µ-SMA, or PCNA were obtained from Sigma, 5 Prime 3 Prime, and Oncogene Sciences. Fluorescent labels were visualized using a dual channel Zeiss microscope and a computer imaging system (Image 1 software). A phase-contrast microscope was utilized to visualize antigens with alkaline phosphatase secondary antibodies (Vector Laboratories). Cytochromes utilized were alkaline phosphatase with fast green as counterstain, and FITC with Evans blue as counterstain (Sigma).

The number of PCNA (+), c-myb(+), or NFkB(+), α-SMA(+) cells was expressed as a percentage of total cells. At least 1,000 cells were analyzed for each experimental point, and a minimum of two observers analyzed each immunohistochemical experiment independently. Negative control samples were processed in parallel under the same conditions, but with omission of the first antibody.

For the experiments of this example, either the Student t or the Fisher's exact test (two-tailed) was used to evaluate the differences of the means between groups, with a P value of less than 0.05 as significant.

B. Inhibition of Hepatic Stellate Cell Activation

The role of lipid peroxidation on stellate cell activation was examined. Stellate cell activation was induced in quiescent cells growing on a EHS matrix; inhibition of this phenotype was evaluated with cells activated by collagen type I matrix. [See Davis et al., J. Biol. Chem. 262:10280–86 (1987)]. When stellate cell activation was induced by TGFα as described, e.g., by Pinzani et al., J. Clin. Invest. 84:1786–93 (1989), a defined media without serum was used. Stellate cell activation was assessed by the expression of α-SMA (as described in Example 1) and S-phase by the presence of PCNA. [Bravo et al., Nature (Lond.) 326:515–17 (1987)].

Figure 5:
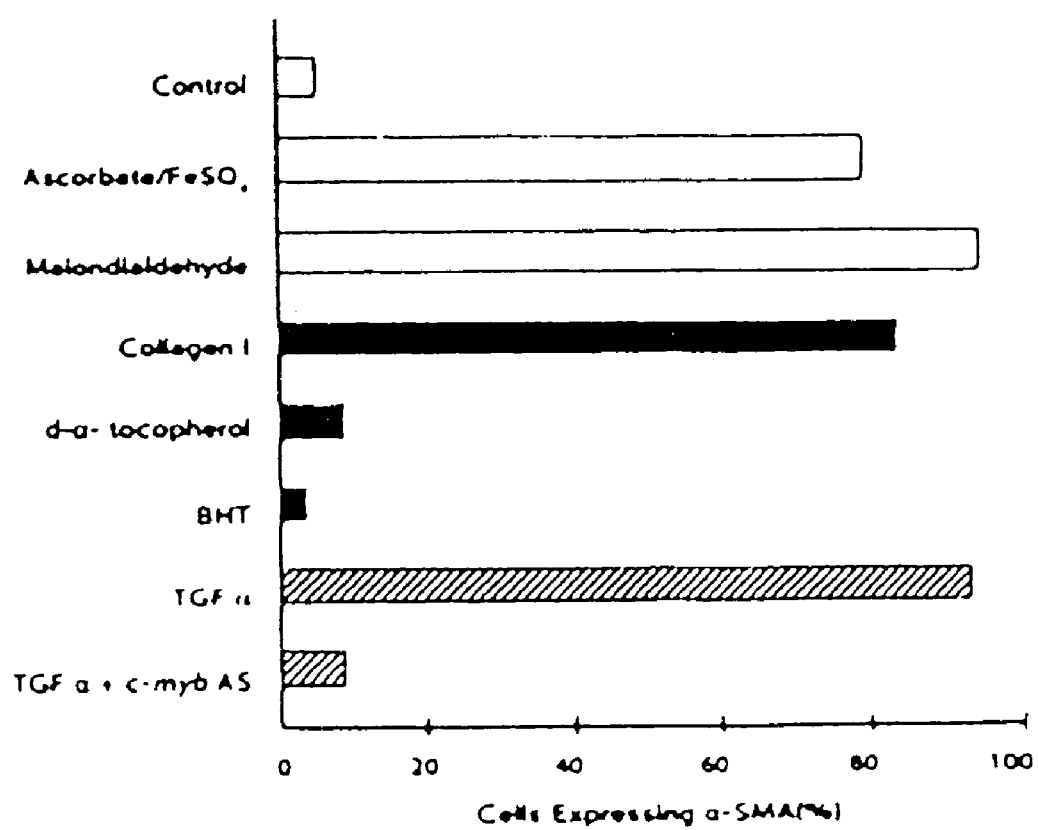
FIG. 5 is a bar graph indicating that oxidative stress induces the expression of α-SMA in cultured hepatic stellate cells and that α-SMA expression is inhibited by vitamin E and butylated hydroxytoluene (BHT).

FIG. 5 is a bar graph indicating that oxidative stress induces the expression of α-SMA in cultured hepatic stellate cells and that α-SMA expression is inhibited by vitamin E and BHT. Referring to FIG. 5, the open bars represent hepatic cells cultured on EHS matrix (control; with ascorbic acid [200 µM]/$FeSO_4$ [50 µM]; and with 200 µM malondialdehyde), the closed bars represent hepatic cells cultured with collagen type I matrix (collagen I; with d-α-tocopherol [50 µM]; and with BHT [50 µM]), and the hatched bars represent hepatic cells cultured with plastic (12 nM TGFα with and without 25 µM c-myb antisense). Values represent the percentage of cells positive for α-SMA (P<0.05 for ascorbic acid/$FeSO_4$, malondialdehyde, collagen and TGFα; SEM<30% of the mean for all conditions).

As depicted by the results in FIG. 5, quiescent stellate cells cultured on an EHS matrix (open bars; control) were activated by the generation of free radicals using ascorbic acid. Whether malondialdehyde would mimic the effects of inducing lipid peroxidation was tested as previous reports indicated that ascorbic acid/$FeSO_4$ induces lipid peroxidation in cultured fibroblasts, with the production of malondialdehyde and 4-hydroxynonenal. As depicted by the results in FIG. 5, malondialdehyde (200 μM) markedly stimulated the activation of hepatic stellate cells (open bars; malondialdehyde); moreover, malondialdehyde at lower concentrations (50 μM) was also able to activate stellate cells, but to a lesser extent (data not shown).

By way of comparison, stellate cells cultured on a collagen type I matrix (FIG. 5, closed bars) or treated with TGFα (FIG. 5, hatched bars) became activated at a much higher rate than their respective control conditions. The values of the control condition for TGFα were comparable to those of the EHS control (<10%). Similarly, stellate cells cultured on plastic and treated with malondialdehyde displayed a more activated pattern than cells grown on plastic [93 vs. 58% of cells (+) for α-SMA; P<0.05]. The fact that the antioxidants d-α-tocopherol and BHT blocked the induction of stellate cell activation by collagen type I matrix indicates that i) oxidative stress plays an important role in stellate cell activation, and ii) that those compounds are effective in reducing stellate cell activation and the hepatic fibrosis to which it has been linked.

Assessment by α-SMA immunohistochemistry indicated the association between oxidative stress and stellate cell activation. Specifically, the expression of α-SMA was markedly induced in stellate cells treated with malondialdehyde when compared to control stellate cells cultured on a EHS matrix (data not shown); a similar stimulation of α-SMA was observed when stellate cells were cultured on collagen type I (data not shown). However, the increased expression of α-SMA was abolished by d-α-tocopherol and BHT, as indicated in FIG. 5.

C. Inhibition of Hepatic Stellate Cell Proliferation

Figure 6:
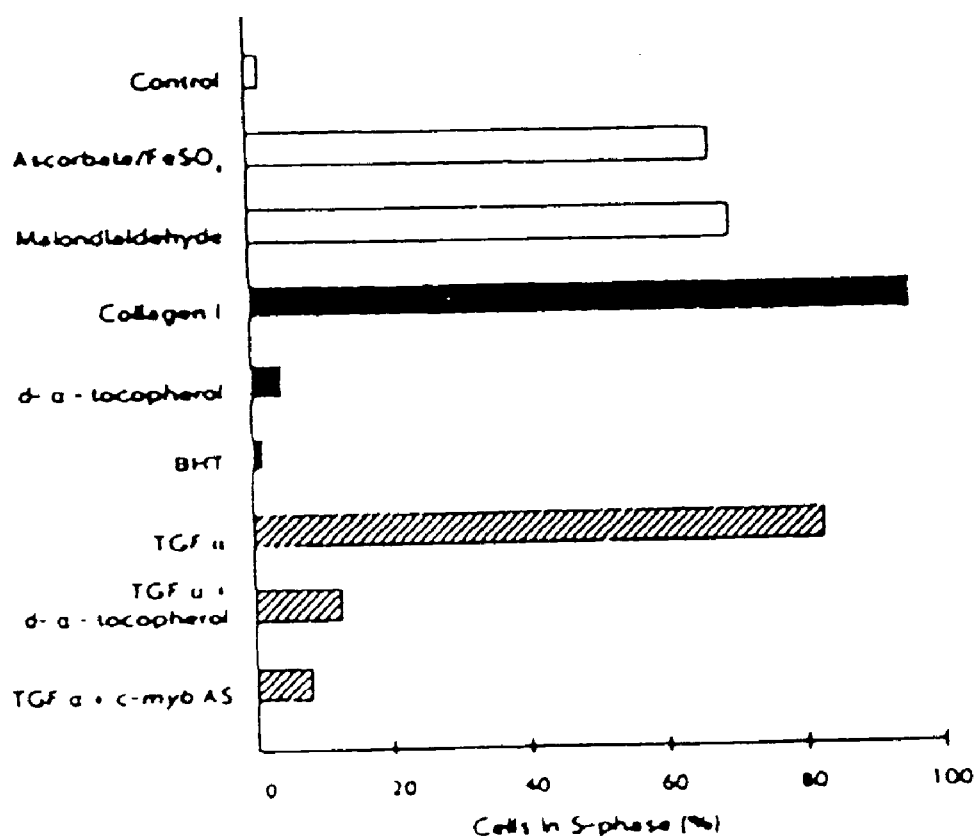
FIG. 6 is a bar graph indicating that oxidative stress induces hepatic stellate cell proliferation, as measured by nuclear expression of proliferating cell nuclear antigen (PCNA) and that proliferation is inhibited by vitamin E and BHT.

FIG. 6 is a bar graph indicating that oxidative stress induces hepatic stellate cell proliferation, as measured by nuclear expression of PCNA, and that proliferation is inhibited by vitamin E and BHT. The nuclear expression of PCNA was detected by immunohistochemistry, as described above, in primary stellate cells. Referring to FIG. 6, the open bars represent hepatic cells cultured on EHS matrix (control; with ascorbic acid [200 μM]/FeSO$_4$ [50 μM]; and with malondialdehyde [200 μM]), the closed bars represent hepatic cells cultured with collagen type I matrix (collagen I; with d-α-tocopherol [50 μM]; and with BHT [50 μM]), and the hatched bars represent hepatic cells cultured with plastic (12 nM TGFα with and without 25 μM c-myb antisense). Values represent the percentage of cells positive for PCNA (P<0.05 for ascorbic acid/FeSO$_4$, malondialdehyde, collagen, and TGFα; SEM<30% of the mean for all conditions).

Control stellate cells on a EHS matrix (open bar, control) or control TGFα stellate cells were quiescent in regard to proliferation, with only approximately 5% of the cells in S-phase. In contrast, oxidative stress induced by ascorbic acid/FeSO$_4$, collagen type I matrix, and TGFα markedly increased stellate cell proliferation, as indicated by the percentage of cells in S-phase in FIG. 6 (>66% for all conditions). Malondialdehyde, a product of lipid peroxidation, also stimulated stellate cell entry into S-phase. However, the antioxidants d-α-tocopherol and BHT, blocked the activation of the stellate cell cycle induced by collagen type I matrix or TGFα.

The results presented in this example indicate that BHT and d-α-tocopherol prevented stellate cell activation and proliferation. Thus, both agents are effective in preventing hepatic fibrosis.

EXAMPLE 3

Antioxidant Treatment Of Chronic Hepatitis C

Enhanced oxidative stress initiates a fibrogenesis cascade in the liver of patients with chronic hepatitis C. The experiments of this example describe potential therapeutic approaches for the prevention of liver fibrosis in chronic hepatitis C.

A. Methodology

Patients and Treatment Regimen

Patients with chronic active hepatitis C and severe necro-inflammatory changes without cirrhosis (as established by liver biopsy) were studied at the University of California San Diego Liver Clinic. Six patients (2 women and 4 men; 47±8 years) who had not responded to interferon α-2b therapy (i.e., who were refractory) and with no other co-morbid illnesses received 1,200 IU/day of d-α-tocopherol orally for 8 weeks. On completion of the study, all patients underwent a liver biopsy; liver sections from patients with chronic hepatitis C and from individuals without liver disease were provided by Dr. C. Behling at UCSD.

Liver tissue obtained from biopsies was studied, as described below, by immunohistochemistry and in situ hybridization with specific riboprobes. Carbonyl modifications were assayed in plasma proteins, as an index of oxidative stress. [Palinski et al., Arteriosclerosis 10:325–35 (1990)]. Serum alanine aminotransferase (ALT) was determined with a (Hitachi) analyzer, plasma d-α-tocopherol by high pressure chromatography, and HCV RNA by quantitative PCR. [See U.S. Pat. Nos. 4,683,202 and 4,683,195, hereby incorporated by reference].

Antisera

Antisera to MDA-lysine adducts were prepared by a variation of the technique described by Houglum et al., J Clin Invest 86:1991–98 (1990). Briefly, rabbit LDS was purified and modified with MDA, and the modified autologous LDL was used to immunize rabbits. The resultant antisera were epitope specific and recognized MDA-lysine adducts on a variety of different proteins but did not react to native albumin.

Immunohistochemistry

Sections from paraffin-embedded blocks were deparaffinized, passed through graded series of alcohol, rehydrated in PBS, and stained with hematoxylin and eosin. Immunohistochemistry was performed using the avidin-biotin complex-alkaline phosphatase, peroxidase systems (Vector Laboratories, ABC-peroxidase system) or fluorescein. Sections were immunostained with antibodies specific for MDA-protein adducts, α-smooth muscle actin (Sigma), or c-myb. [See Houglum et al., J. Clin. Invest. 96:2269–76 (1995)].

The antisera was used with flurochrome-conjugated secondary antibodies. Fluorescent labels were visualized using a dual filter Zeiss microscope, while a phase-contrast microscope was used to visualize antigens with hematoxilin/eosin or alkaline phosphatase secondary antibodies.

In Situ Hybridization

Hybridization, RNase digestion of mismatched sequences, and immunological detection of the digoxigenin-labeled RNA probes were performed as described by Houglum et al., Am. J. Phys 267:G908–913 (1994). Briefly, single stranded RNA probes in both sense and antisense orientations were transcribed in vitro from the plasmid $_p$HuCol, which contains a 300 base pair cDNA fragment of the human collagen α1(I) gene, and labeled with digoxigenin-11-UTP. Plasmid HF677, which contains a 1.8 kb cDNA fragment of the human collagen α1(I) gene, is available from the American Type Culture Collection ("ATCC") under accession numbers 61322. For the labelling procedure, 2 μg of linearized plasmid were transcribed in a 30 μL reaction volume containing 40 mM tris (hydroxymethyl)aminomethane (Tris)•HCl, pH 7.9; 6 mM $MgCl_2$; 2 mM aperrnidine•HCl; 10 mM dithiothreitol, 10 mM ATP, CTP, and GTP; 6.5 mM UTP; and 3.5 mM digoxigenin-11-UTP with 309 units of T3 or T7 DNA polymerase. The specificity of the probe was assessed by in situ hybridization of human skin. All sections were processed using same batches of probe and reagents and using sense and antisense in parallel.

Figure 7A:
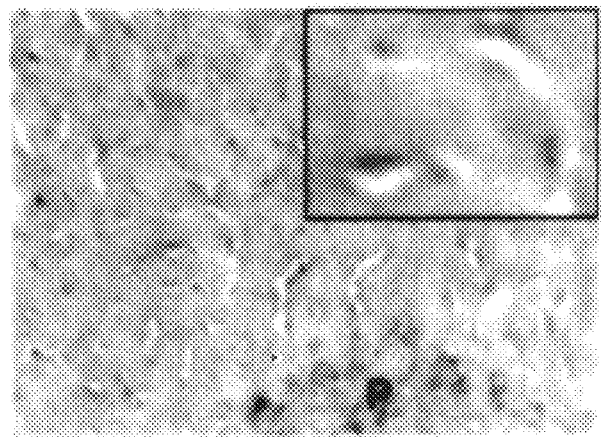
FIGS. 7A and 7B are photographs depicting the extent of MDA-protein adducts in representative examples of liver sections (×125) before (FIG. 7A) and after (FIG. 7B) treatment with d-α-tocopherol in a patient with chronic hepatitis C.

B. Immunohistological Findings And In Situ Hybridization Prior To d-α-Tocopherol Treatment On hematoxylin/eosin stained liver sections, the extent of hepatic necrosis and inflammation was severe in all patients prior to treatment. As indicated above, the presence of MDA-protein adducts, an index of lipid peroxidation, was detected with antibodies specific against MDA-lysine epitopes. These protein adducts were negligible in liver sections from individuals without liver disease (not shown), but prominent in areas with active inflammation in liver sections from patients with chronic hepatitis C (FIG. 7A). The MDA-protein adducts were conspicuous in the septae and sinusoids. No staining was detected when the first antibody was omitted.

Stellate cells that exhibited enhanced oxidative stress (MDA-adducts) were 1 5 activated since they adopted a myofibroblastic phenotype and expressed α-smooth muscle actin (FIG. 7C); by comparison, activation of stellate cells was rarely observed in normal liver sections (not shown).

Figure 7B:
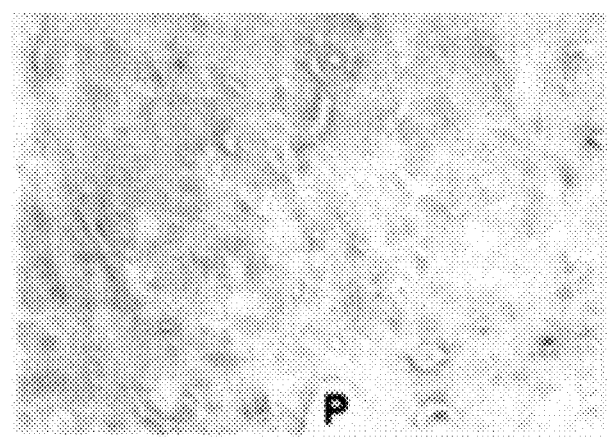
Figure 7C:
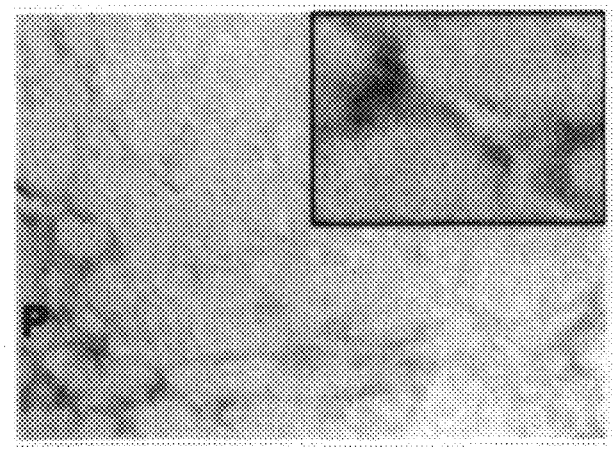
FIGS. 7C and 7D are photographs depicting the extent of α-SMA expression in representative examples of liver sections (×125) before (FIG. 7C) and after (FIG. 7D) treatment with d-α-tocopherol in a patient with chronic hepatitis C.
Figure 7D:
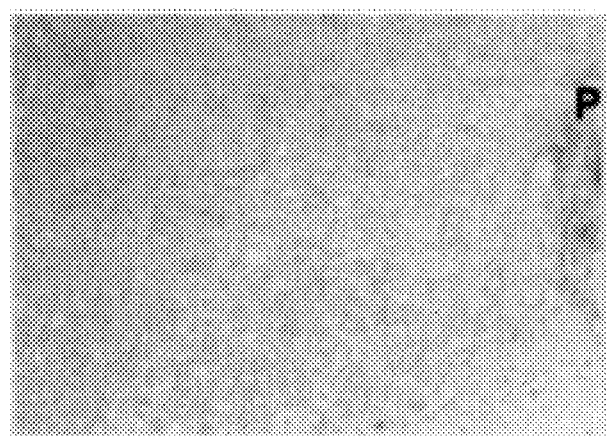
Figure 7E:
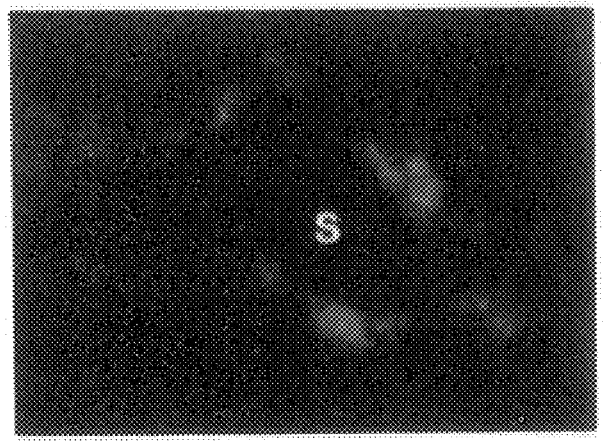
FIGS. 7E and 7F are photographs depicting the extent of c-myb in representative examples of liver sections (×600) before (FIG. 7E) and after (FIG. 7F) treatment with d-α-tocopherol in a patient with chronic hepatitis C.

As set forth above, activation of cultured primary stellate cells is mediated by oxidative stress and MDA, at least in part through the nuclear expression of the transcription factor c-myb. The nuclear expression of c-myb was induced in activated stellate cells, as detected with a monoclonal antibody against the carboxyterminal domain (FIG. 7E). The nuclear expression of c-myb was minimal in stellate cells of normal liver sections (not shown).

Figure 7F:
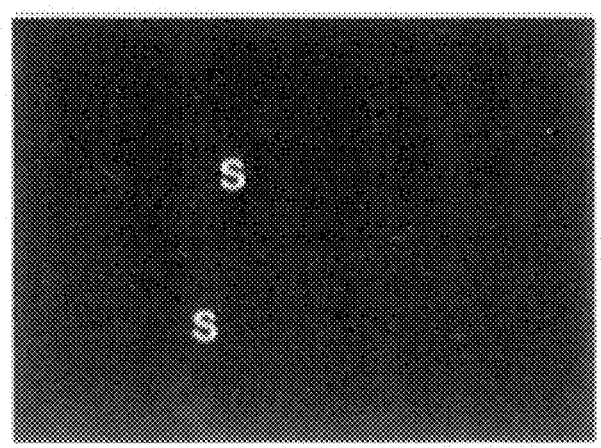
Figure 7G:
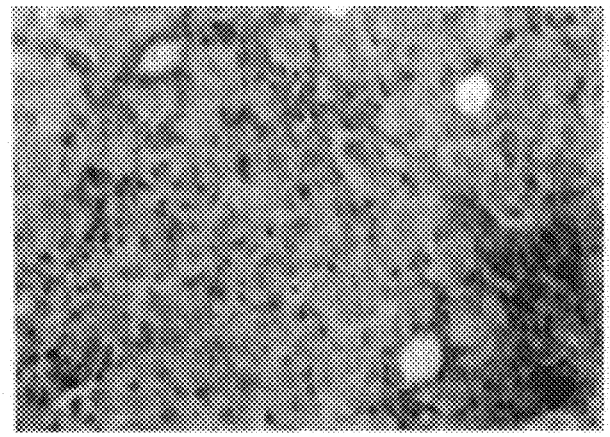
FIGS. 7G and 7H are photographs depicting in situ hybridization of $\alpha_1(I)$ mRNA in representative examples of liver sections (×125) before (FIG. 7G) and after (FIG. 7H) treatment with d-α-tocopherol in a patient with chronic hepatitis C.
Figure 7H:
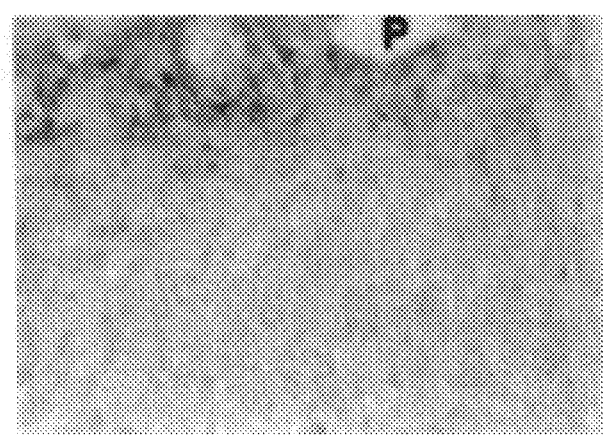

Tests were also performed to determine whether excessive transcription of the collagen α1(I) gene by activated stellate cells, a key step in experimental hepatic fibrosis, occurs in chronic hepatitis C. Collagen α1(I) mRNA was increased in activated stellate cells by in situ hybridization with a specific antisense riboprobe (FIG. 7G). In contrast, collagen α1(I) mRNA was minimally detected in the parenchyma of liver sections from control individuals hybridized with the antisense probe alone but it was positive, as expected, in the portal triads (not shown). RNase treatment (negative control) prevented detection of collagen α1(I) mRNA in the liver sections.

C. Immunohistological Findings And In Situ Hybridization Subsequent To d-α-Tocopherol Treatment Because of the evidence supporting an oxidative stress pathway leading to active fibrogenesis in chronic hepatitis C, six of the patients, who were refractory to interferon therapy, were treated with d-α-tocopherol (1,200 IU/day) for 8 weeks. Treatment resulted in higher plasma levels of d-α-tocopherol compared with before treatment values (9.6±4.3vs27±6.8;P<0.003). Moreover, after d-α-tocopherol treatment, liver sections showed an inhibition of the fibrogenesis cascade, including (i) decreased MDA-adducts, particularly in the sinusoids (FIG. 7B); (ii) a lesser degree of stellate cell activation (FIG. 7D); (iii) diminished expression of c-myb in stellate cells (FIG. 7F); and (iv) lower expression of collagen α1(I) mRNA in stellate cells (FIG. 7G).

In addition, treatment with d-α-tocopherol decreased the carbonyl modified plasma proteins (2.7±0.4vs.1.5±0.4μmol/mL;P<0.001), a sensitive index of oxidative stress. However, after 8 weeks, d-α-tocopherol treatment did not significantly affect the serum ALT levels, (135±59vs.101±36 U/mL), HCV titres or the histologic degree of hepatocellular inflammation (not shown).

The results presented above indicate that stellate cell activation and collagen production, the basis of hepatic fibrosis, can be inhibited by d-α-tocopherol in patients with chronic hepatitis C. Thus, antioxidant therapy is beneficial in preventing the development of hepatic fibrosis in chronic hepatitis C.

From the above, it should be evident that the present invention describes effective alternative methods for the treatment and prevention of hepatic fibrosis and viral hepatitis C. These methods are especially contemplated for use with patients who have not responded to alternative therapies, including patients refractory to interferon therapy.

---

We claim:

1. A method of treating hepatic fibrosis, comprising:

a) providing i) a subject with hepatic fibrosis, and ii) butylated hydroxytoluene; and b) administering a therapeutic amount of said butylated hydroxytoluene under conditions such that said hepatic fibrosis is diminished.

2. The method of claim 1, wherein said butylated hydroxytoluene is administered orally to said subject.

* * * * *